United States Patent
Connors et al.

(10) Patent No.: US 12,416,024 B2
(45) Date of Patent: Sep. 16, 2025

(54) BIOLOGICALLY ENHANCED OIL RECOVERY METHODS

(71) Applicant: Transworld Technologies Inc., Houston, TX (US)

(72) Inventors: Daniel Edward Connors, Denver, CO (US); Jordan Andrew Bradfish, Thornton, CO (US); Roland Peter DeBruyn, Highlands Ranch, CO (US); Helen Mitchell, Denver, CO (US); Joseph Edward Zemetra, Lakewood, CO (US)

(73) Assignee: Transworld Technologies Inc., Houston, TX (US)

( * ) Notice: Subject to any disclaimer, the term of this patent is extended or adjusted under 35 U.S.C. 154(b) by 590 days.

(21) Appl. No.: 15/940,692

(22) Filed: Mar. 29, 2018

(65) Prior Publication Data
US 2019/0300912 A1   Oct. 3, 2019

(51) Int. Cl.
*E21B 43/16* (2006.01)
*C12P 5/02* (2006.01)

(52) U.S. Cl.
CPC ............ *C12P 5/023* (2013.01); *E21B 43/166* (2013.01)

(58) Field of Classification Search
CPC ............................. E21B 43/166; C12P 5/023
USPC ....................................................... 166/246
See application file for complete search history.

(56) References Cited

U.S. PATENT DOCUMENTS

| | | |
|---|---|---|
| 1,990,523 A | 2/1935 | Buswell et al. |
| 2,185,216 A | 1/1940 | McManus et al. |
| 2,413,278 A | 12/1946 | Zobell |
| 2,641,566 A | 6/1953 | Zobell |
| 2,659,659 A | 11/1953 | Schmidl |
| 2,660,550 A | 11/1953 | Updegraff et al. |
| 2,807,570 A | 9/1957 | Updegraff |
| 2,907,389 A | 10/1959 | Hitzman |
| 2,975,835 A | 3/1961 | Bond |
| 3,006,755 A | 10/1961 | Adams |
| 3,185,216 A | 5/1965 | Hitzman |
| 3,332,487 A | 7/1967 | Jones |

(Continued)

FOREIGN PATENT DOCUMENTS

| | | |
|---|---|---|
| CN | 1447010 A | 10/2003 |
| DE | 4036787 A1 | 5/1992 |

(Continued)

OTHER PUBLICATIONS

Brink et al., "The Geochemical Evolution of Water Coproduced with Coalbed Natural Gas in the Powder River Basin, Wyoming," Environmental Geosciences, V. 15, No. 4 (Dec. 2008), pp. 153-171.*

(Continued)

*Primary Examiner* — Silvana C Runyan
(74) *Attorney, Agent, or Firm* — Kilpatrick Townsend & Stockton LLP (57) ABSTRACT

Methods of enhancing oil recovery may include accessing a consortium of microorganisms in a geologic formation that includes oil. The methods may include delivering an aqueous material incorporating dissolved hydrogen to the consortium of microorganisms. The methods may include increasing production of gaseous materials by the consortium of microorganisms. The methods may also include recovering oil from the reservoir.

20 Claims, 4 Drawing Sheets

(56) References Cited

U.S. PATENT DOCUMENTS

| | | | |
|---|---|---|---|
| 3,340,930 A | 9/1967 | Hitzman | |
| 3,437,654 A | 4/1969 | Dix | |
| 3,637,686 A | 1/1972 | Kokubo et al. | |
| 3,640,846 A | 2/1972 | Johnson | |
| 3,724,542 A | 4/1973 | Hamilton | |
| 3,800,872 A | 4/1974 | Friedman | |
| 3,826,308 A | 7/1974 | Compere | |
| 3,982,995 A | 9/1976 | Yen et al. | |
| 4,184,547 A | 1/1980 | Klass et al. | |
| 4,300,632 A | 11/1981 | Wilberger et al. | |
| 4,316,961 A | 2/1982 | Klass et al. | |
| 4,329,428 A | 5/1982 | Ghosh et al. | |
| 4,349,633 A | 9/1982 | Worne et al. | |
| 4,358,535 A | 11/1982 | Falkow et al. | |
| 4,358,537 A | 11/1982 | Chynoweth | |
| 4,386,159 A | 5/1983 | Kanai | |
| RE31,347 E | 8/1983 | Reijonen et al. | |
| 4,416,332 A | 11/1983 | Wiberger et al. | |
| 4,424,064 A | 1/1984 | Klass et al. | |
| 4,446,919 A | 5/1984 | Hitzman | |
| 4,450,908 A | 5/1984 | Hitzman | |
| 4,475,590 A | 10/1984 | Brown | |
| 4,481,293 A | 11/1984 | Thomsen et al. | |
| 4,522,261 A | 6/1985 | McInerney et al. | |
| 4,562,156 A | 12/1985 | Isbister et al. | |
| 4,579,562 A | 4/1986 | Tarman et al. | |
| 4,610,302 A | 9/1986 | Clark | |
| 4,640,767 A | 2/1987 | Zajic et al. | |
| 4,648,458 A | 3/1987 | Broadas | |
| 4,666,605 A | 5/1987 | Minami et al. | |
| 4,678,033 A | 7/1987 | Killough | |
| 4,743,383 A | 5/1988 | Stewart et al. | |
| 4,799,545 A | 1/1989 | Silver et al. | |
| 4,826,769 A | 5/1989 | Menger | |
| 4,845,034 A | 7/1989 | Menger et al. | |
| 4,883,753 A | 11/1989 | Belaich et al. | |
| 4,905,761 A | 3/1990 | Bryant | |
| 4,906,575 A | 3/1990 | Silver et al. | |
| 4,914,024 A | 4/1990 | Strandberg et al. | |
| 4,947,932 A | 8/1990 | Silver et al. | |
| 4,969,130 A | 11/1990 | Wason et al. | |
| 4,971,151 A | 11/1990 | Sheehy | |
| 5,044,435 A | 9/1991 | Sperl et al. | |
| 5,076,927 A | 12/1991 | Hunter | |
| 5,081,023 A | 1/1992 | Yaginuma et al. | |
| 5,083,610 A | 1/1992 | Sheehy | |
| 5,083,611 A | 1/1992 | Clark et al. | |
| 5,087,558 A | 2/1992 | Webster, Jr. | |
| 5,100,553 A | 3/1992 | Nomura et al. | |
| 5,155,042 A | 10/1992 | Lupton et al. | |
| 5,163,510 A | 11/1992 | Sunde | |
| 5,250,427 A | 10/1993 | Weaver et al. | |
| 5,297,625 A * | 3/1994 | Premuzic | C09K 8/58 |
| | | | 166/246 |
| 5,327,967 A | 7/1994 | Jenneman et al. | |
| 5,340,376 A | 8/1994 | Cunningham | |
| 5,341,875 A | 8/1994 | Jenneman et al. | |
| 5,350,684 A | 9/1994 | Nakatsugawa et al. | |
| 5,360,064 A | 11/1994 | Jenneman et al. | |
| 5,363,913 A | 11/1994 | Jenneman et al. | |
| 5,368,099 A | 11/1994 | Davey et al. | |
| 5,424,195 A | 6/1995 | Volkwein | |
| 5,470,823 A | 11/1995 | Williams et al. | |
| 5,490,634 A | 2/1996 | Jain et al. | |
| 5,492,828 A | 2/1996 | Premuzic et al. | |
| 5,500,123 A | 3/1996 | Srivastava | |
| 5,510,033 A | 4/1996 | Ensley et al. | |
| 5,516,971 A | 5/1996 | Hurley | |
| 5,538,530 A | 7/1996 | Heaton et al. | |
| 5,551,515 A | 9/1996 | Fodge et al. | |
| 5,560,737 A | 10/1996 | Schuring et al. | |
| 5,593,886 A | 1/1997 | Gaddy | |
| 5,593,888 A | 1/1997 | Glaze et al. | |
| 5,597,730 A | 1/1997 | Aust et al. | |
| 5,601,700 A | 2/1997 | Bridge et al. | |
| 5,630,942 A | 5/1997 | Steiner | |
| 5,670,345 A | 9/1997 | Srivastava et al. | |
| 5,695,641 A | 12/1997 | Cosulich et al. | |
| 5,723,597 A | 3/1998 | Kohne | |
| 5,763,736 A | 6/1998 | Daume | |
| 5,766,929 A | 6/1998 | Orolin et al. | |
| 5,783,081 A | 7/1998 | Gaddy | |
| 5,821,111 A | 10/1998 | Grady et al. | |
| 5,854,032 A | 12/1998 | Srivastava et al. | |
| 5,858,766 A * | 1/1999 | Premuzic | C09K 8/58 |
| | | | 435/245 |
| 5,885,825 A | 3/1999 | Lin et al. | |
| 5,919,696 A | 7/1999 | Ikeda et al. | |
| 5,928,864 A | 7/1999 | Kohne | |
| 5,955,261 A | 9/1999 | Kohne | |
| 5,955,262 A | 9/1999 | Kourilsky et al. | |
| 6,090,593 A | 7/2000 | Fleming et al. | |
| 6,143,534 A | 11/2000 | Menger et al. | |
| 6,202,051 B1 | 3/2001 | Woolston | |
| 6,210,955 B1 | 4/2001 | Hayes | |
| 6,265,205 B1 | 7/2001 | Hitchens et al. | |
| 6,340,581 B1 | 1/2002 | Gaddy | |
| 6,348,639 B1 | 2/2002 | Crawford et al. | |
| 6,420,594 B1 | 7/2002 | Farone et al. | |
| 6,543,535 B2 | 4/2003 | Converse et al. | |
| 6,546,962 B1 * | 4/2003 | Sunde | E21B 43/16 |
| | | | 137/893 |
| 6,758,270 B1 | 7/2004 | Sunde et al. | |
| 6,795,922 B2 | 9/2004 | Johnson et al. | |
| 6,859,880 B2 | 2/2005 | Johnson et al. | |
| 7,124,817 B1 | 10/2006 | Sunde | |
| 7,426,960 B2 | 9/2008 | Pfeiffer et al. | |
| 7,484,560 B2 * | 2/2009 | Lal | C12R 1/01 |
| | | | 166/246 |
| 7,640,978 B2 * | 1/2010 | Pfeiffer | C12P 3/00 |
| | | | 166/246 |
| 7,696,132 B2 | 4/2010 | Pfeiffer et al. | |
| 7,845,403 B2 | 12/2010 | Pfeiffer et al. | |
| 7,975,762 B2 | 7/2011 | Pfeiffer et al. | |
| 7,977,282 B2 | 7/2011 | Pfeiffer et al. | |
| 8,051,908 B2 | 11/2011 | Pfeiffer et al. | |
| 8,092,559 B2 | 1/2012 | Debryun et al. | |
| 8,302,683 B2 | 11/2012 | Pfeiffer et al. | |
| 8,770,282 B2 | 7/2014 | Pfeiffer et al. | |
| 8,794,315 B2 | 8/2014 | Pfeiffer et al. | |
| 9,057,082 B2 | 6/2015 | Debruyn et al. | |
| 9,458,375 B2 | 10/2016 | Pfeiffer et al. | |
| 2001/0045279 A1 | 11/2001 | Converse et al. | |
| 2002/0102676 A1 | 8/2002 | Zhang et al. | |
| 2003/0062270 A1 | 4/2003 | McAlister | |
| 2003/0098149 A1 | 5/2003 | Wellington et al. | |
| 2003/0205458 A1 | 11/2003 | Roychowdhury | |
| 2003/0209340 A1 | 11/2003 | McClung, III | |
| 2003/0216353 A1 | 11/2003 | Mosher et al. | |
| 2003/0232423 A1 | 12/2003 | Priester et al. | |
| 2004/0033557 A1 | 2/2004 | Scott et al. | |
| 2004/0035785 A1 | 2/2004 | Rebholz | |
| 2004/0164971 A1 | 8/2004 | Hayward et al. | |
| 2004/0228833 A1 | 11/2004 | Costantino et al. | |
| 2005/0053955 A1 | 3/2005 | Sowlay et al. | |
| 2005/0205260 A1 | 9/2005 | McClung, III | |
| 2005/0269261 A1 | 12/2005 | Sublette | |
| 2006/0025465 A1 | 2/2006 | Juujarvi et al. | |
| 2006/0045279 A1 | 3/2006 | Borovitski | |
| 2006/0219403 A1 | 10/2006 | Steinberg | |
| 2006/0223153 A1 | 10/2006 | Pfeiffer et al. | |
| 2006/0223159 A1 | 10/2006 | Pfeiffer et al. | |
| 2006/0223160 A1 * | 10/2006 | Vanzin | C12N 15/1003 |
| | | | 435/252.4 |
| 2006/0237097 A1 | 10/2006 | Lau et al. | |
| 2006/0254765 A1 * | 11/2006 | Pfeiffer | E21B 43/40 |
| | | | 166/246 |
| 2006/0292684 A1 | 12/2006 | Bentley et al. | |
| 2007/0092930 A1 | 4/2007 | Lal et al. | |
| 2007/0151729 A1 | 7/2007 | Hoch et al. | |
| 2007/0248531 A1 | 10/2007 | Debryun et al. | |
| 2007/0261843 A1 * | 11/2007 | Pfeiffer | C12P 5/023 |
| | | | 166/246 |
| 2007/0295505 A1 | 12/2007 | Pfeiffer et al. | |

(56) References Cited

U.S. PATENT DOCUMENTS

| | | | |
|---|---|---|---|
| 2008/0289816 | A1 | 11/2008 | Pfeiffer et al. |
| 2008/0299635 | A1 | 12/2008 | Pfeiffer et al. |
| 2010/0035309 | A1 | 2/2010 | Haveman et al. |
| 2010/0101782 | A1 | 4/2010 | Pfeiffer et al. |
| 2010/0190203 | A1 | 7/2010 | Pfeiffer et al. |
| 2010/0248321 | A1 | 9/2010 | Steaffens et al. |
| 2010/0248322 | A1 | 9/2010 | Pfeiffer et al. |
| 2010/0300680 | A1 | 12/2010 | Pfeiffer et al. |
| 2011/0139439 | A1 | 6/2011 | Dannar et al. |
| 2011/0244541 | A1 | 10/2011 | Zitomer |
| 2011/0250582 | A1 | 10/2011 | Gates et al. |
| 2011/0277991 | A1 | 11/2011 | Toledo et al. |
| 2011/0283604 | A1 | 11/2011 | Foster et al. |
| 2011/0284215 | A1 | 11/2011 | Pfeiffer et al. |
| 2013/0240204 | A1 | 9/2013 | Pfeiffer et al. |
| 2014/0034297 | A1* | 2/2014 | Mahaffey ............ C09K 8/58 166/246 |
| 2015/0053407 | A1* | 2/2015 | Voordouw ......... E21B 43/2406 166/308.2 |
| 2015/0101816 | A1 | 4/2015 | Pfeiffer et al. |
| 2015/0104795 | A1 | 4/2015 | Pfeiffer et al. |
| 2017/0240806 | A1 | 8/2017 | Pfeiffer et al. |

FOREIGN PATENT DOCUMENTS

| | | |
|---|---|---|
| DE | 4115435 C1 | 6/1992 |
| DE | 19520548 A1 | 12/1996 |
| JP | 09121868 A | 5/1997 |
| WO | 197900201 A1 | 4/1979 |
| WO | 198910463 A1 | 11/1989 |
| WO | 199213172 A1 | 8/1992 |
| WO | 200168904 A1 | 9/2001 |
| WO | 200206503 A1 | 1/2002 |
| WO | 200234931 A2 | 5/2002 |
| WO | 2004071195 A1 | 8/2004 |
| WO | 2005115648 A1 | 12/2005 |
| WO | 2005115649 A1 | 12/2005 |
| WO | 2006118569 A1 | 11/2006 |
| WO | 2006118570 A1 | 11/2006 |
| WO | 2007022122 A2 | 2/2007 |
| WO | 2007/118094 A2 | 10/2007 |
| WO | 2008/067227 A1 | 6/2008 |
| WO | 2018-015224 A1 | 1/2018 |

OTHER PUBLICATIONS

Aitken et al., "Anaerobic hydrocarbon degradation in deep subsurface oil reserves" NATURE, Sep. 16, 2004, pp. 291-294, 4 pages.
Anderson et al., "Hexadecane Decay by Methanogenesis", NATURE, v. 404, p. 722, Apr. 13, 2000, 2 pages.
Anderson et al., "Anaerobic Benzene Oxidation in the Fe(III) Reduction Zone of Petroleum-Contaminated Aquifers", Environmental Science & Technology, vol. 32, No. 9, pp. 1222-1229, Mar. 18, 1998, 8 pages.
Artech Inc., "Biological Gasification of Coals. Final Report", U.S. Department of Energy, Contract DE-AC21-87MC23285, pp. 40-63, Mar. 1990, 27 pages.
Author Unknown, "Chapter 4: Hydraulic Fracturing Fluids," Evaluation of Impacts to Underground Sources of Drinking Water by Hydraulic Fracturing of Coalbed Methane Reservoirs, U.S. Environmental Protection Agency, Jun. 2004, 26 pages.
Basiliko et al., "Influence of Ni, Co, Fe, and Na additions on methane production in Sphagnum dominated Northern American peatlands" Biogeomochmistry, vol. 52: 133-153, 2001, 21 pages.
Batelle and Duke Engineering and Services; *Surfactant-Enhanced Aquifer Remediation (SEAR) Design Manual*; NFESC Technical Report TR-2206-ENV, Apr. 2002, all pgs: entire document; Naval Facilities Engineering Command Washington, DC 20374-5065 USA.
Belyaev et al., "Methanogenic Bacteria from the Bondyuzhskoe Oil Field: General Characterization and Analysis of Stable-Carbon Isotopic Fractionation" Applied and Environmental Microbiology, V. 45, No. 2, pp. 691-697, Feb. 1983, 7 pages.

Bernard et al., "Indigenous Microorganisms in Connate Water of Many Oil Fields: A New Tool in Exploration and Production Techniques" SPE 24811, pp. 467-476, 1992, 10 pages.
Biville et al., "In vivo positive effects of exogenous pyrophosphate on Escherichia coli cell growth and stationary phase survival", Res. Microbiol. V. 147, pp. 597-608, 1996, 12 pages.
Boone et al., "Bergey's Manual of Systematic Bacteriology-Second Edition- vol. One ", The Archaea and the Deeply Branching and Phototrophic Bacteria, SPRINGER, 2001, 4 pages.
R. Boopathy, "Anaerobic degradation of No. 2 diesel fuel in the wetland sediments od Barataria- Terrebone estuary under various electron acceptor conditions," Bioresource Technology, vol. 86, pp. 171-175, 2003, 5 pages.
Brauer, S. et al., "Methanogenesis in McLean Bog, an Acidic Peat Bog in Upstate New York: Stimulation by H2/CO2 in the Presence of Rifampicin, or by Low Concentrations of Acetate," (Geomicrobiology Journal, Oct.-Nov. 2004, vol. 21, No. 7, pp. 433-443(11)), http://www.ingentaconnect.com, printed Apr. 26, 2005, all pgs.
Braun, Harry, "The Bad News About Natural Gas," Hydrogen News, Mar. 15, 2003, all pgs.
Brockman, Fred "Regulation of Microbial Communities" at http://www.sysbio.org/sysbio/microbial/index.stm, 2005, all pages.
Brown, L.R., and Vadie, A.A., "Slowing Production Decline and Extending the Economic Life of an Oil Field: New MEOR Technology", SPE 59306; SPE/DOE Improved Oil Recovery Symposium, Tulsa, Oklahoma, Apr. 3-5, 2000, all pages.
Budwill, Karen "Microbial Methanogenesis and its Role in Enhancing Coalbed Methane Recovery" (Canadian Coals) CSEG Recorder (Nov. 2003) pp. 41-43.
Business Wire, "U.S. Microbics opens new profit center to outside customers; Bug factory brews microbe colonies for third party applications," Apr. 26, 2005, p. 1, all pgs.
CAN Europe, "Climate technology sheet #9: Hydrogen production," published Nov. 2003, pp. 1-10.
Cervantes, Francisco J et al., "Competition between methanogenesis and quinone respiration for ecologically important substrates in anaerobic consortia" FEMS Microbiology Ecology 34, 2000, pp. 161-171.
Claypool, George E. "Geochemical Characterization of Biogenic Gas and Coalbed Methane in Shallow Gas Fields: Eastern Denver Basin, Powder River Basin and Williston Basin" Luca Technologies, Inc. Internal Report, Jul. 8, 2001, all pages.
Clayton et al. "Oil-Generating Coals of the San Juan Basin, New Mexico and Colorado, U.S." Org. Geochem. 1991, pp. 735-742, vol. 17, No. 6.
Clayton, C. et al. "Source Volumetrics of Biogenic Gas Generation" Bacterial Gas, Ed. R. Vially, 1992, pp. 191-204, Paris.
Coates, John D., Anderson, Robert T., et al., "Anaerobic Hydrocarbon Degradation in Petroleum- Contaminated Harbor Sediments under Sulfate-Reducing and Artificially Imposed Conditions", Environ. Sci. Technol., vol. 30, No. 9, pp. 2784-2789, 1996.
Connan, J. et al. Anaerobic biodegradation of petroleum in reservoirs: a widespread phenomenon in nature: 18th International Meeting on Organic Geochemistry Sep. 22-26, 1997 Maastricht, The Netherlands (Abstr.), p. 02: 5-6.
Connan, J. et al. "Origin of Gases in Reservoirs" 1995 International Gas Research Conference, 1996, pp. 21-41.
Conrad, R. "Contribution of hydrogen to methane production and control of hydrogen concentrations in methanogenic soils and sediments" FEMS Microbiology Ecology, 28 (1999) pp. 193-202.
Debruin, R.H. et al. "Coalbed Methane In Wyoming" Wyoming State Geological Survey (Laramie, WY), Information Pamphlet 7 (second revision), 2004, all pages.
Donaldson et al., "Conference Focuses on Microbial Enhancement of Oil Recovery," The Oil and Gas Journal, pp. 47-52, Dec. 20, 1982.
Donaldson, Eric C. et al. Microbial Enhanced Oil Recovery, Developments in Petroleum Science, 1989, v. 22, pp. 1-14, 121, 123, 149, Elsevier.
Dong, Wen-Sheng et al., "Hydrogen Production from Methane Reforming Reactions over Ni/MgO Catalyst," Bull. Korean Chem. Soc. 2001, vol. 22, No. 12, Aug. 11, 2001, all pgs.

(56) References Cited

OTHER PUBLICATIONS

Dumitru, Razvan et al., "Targeting Methanopterin Biosynthesis To Inhibit Methanogenesis," Applied and Environmental Microbiology, vol. 69, No. 12, Dec. 2003, pp. 7236-7241.
Elias, Paul, "Mining for single-celled gold; Biotechs looking for cash in on Mother Nature's creations" Jul. 4, 2004, San Antonio Express-News, p. 3L, all pgs.
Faber, E. et al. "Distinction of Bacterial and Thermogenic Hydrocarbon Gases" Bacterial Gas, Ed. R. Vially, 1992, pp. 63-74, Paris.
Ferry et al. 1976. Anaerobic Degradation of Benzoate to Methane by Microbial Consortium. Arch. Microbiol. 107, pp. 33-40.
Ficker et al., "Molecular Characterization of a Toluene-Degrading Methanogenic Consortium," Applied and Environmental Microbiology, Dec. 1999, vol. 65, pp. 5576-5585.
Flesner, R. et al. "Pilot-scale base hydrolysis processing of HMX-based plastic-bonded explosives", 4th International Symposium on Special Topics in Chemical Propulsion: Challenges In Propellants and 100 Years After Nobel, May 27-31, 1996, pp. 213-220.
Gaasterland, Terry "Archaeal Genomics" Current Opinions in Microbiology (1999) 2:542-547.
Galagan, James, E. et al. "The Genome of M. acetivorans Reveals Extensive Metabolic and Physiological Diversity" Genome Research 12: 532-542 (2002).
Gencic, S. et al. "Two separate one-electron steps in the reductive activation of the A cluster in subunit beta of the ACDS complex in Methanosarcina thermophilia." Biochemistry, May 20, 2008; 47(20): 5544-55. (Abstract).
Gilcrease, P., et al., "Making microbial methane work: The potential for new biogenic gas," WorldOil, Nov. 2007 [retrieved on Aug. 8, 2011], all pages, vol. 228 No. 11, retrieved from http://www.worldoil.com/November-2007-Making-microbial-methane-work-The-potential-for-new-biogenics-gas.html.
Grbic-Galic, D., and Vogel, T. "Transformation of Toluene and Benzene by mixed methanogenic cultures" Applied and Environmental Microbiology, 1987, v. 53, pp. 254-260.
Groudeva, V. I. et al. "Enhanced Oil Recovery by Stimulating the Activity of the Indigenous Microflora of Oil Reservoirs": Biohydrometallurgical Technologies (Eds. Torma, A. E., Apel, M.L.; and Brierlay, C.L.): Minerals, Metals, & Mater. Soc. Biohydromet. Technol. Int. Symp, 1993 (Jackson Hole, Wy. 93.8.22-25) Proc., v. 2, pp. 349-356.
Gullapalli, Irene L. et al., "Laboratory Design and Field Implementation of Microbial Profile Modification Process", SPE Reservoir Evaluation & Engineering, v. 3, No. 1, pp. 42-49, Feb. 2000.
Halbouty, M.T. "East Texas Field--USA, East Texas Basin, Texas; in Stratigraphic Traps II" (compiled by N.H. Foster, and E.A. Beaumont) AAPG Treatise of Petroleum Geology, Atlas of Oil and Gas Fields, 1991, pp. 189-206.
Hales, B.A et al. "Isolation and Identification of Methanogen-specific DNA from Blanket Bog Peat by PCR Amplification and Sequence Analysis", Applied and Environmental Microbiology, 1996, pp. 668-675.
Hattori, Satoshi et al.; "Thermacetogenium phaeum gen.nov.,sp. nov., a strictly anaerobic, thermophilic, syntrophic acetate-oxidizing bacterium", Internation. Journal of Systematic and Evolutionary Microbiology (2000), 50, 1601-1609, all p. 2000.
Hunkeler et al., "Petroleum Hydrocarbon Mineralization in Anaerobic Laboratory Aquifer Columns," Journal of Contaminant Hydrology 32, pp. 41-61, 1998.
Hydrogen production in oil field production fluids with inactive methanogens. Data to be considered for incorporation into Luca's hydrogen patent, unauthored text, Mar. 9, 05, all pgs.
Intera In. and Naval Facilities Engineering Service Center; *Surfactant-Enhanced Aquifer Remediation (SEAR) Implementation Manual*; NFESC Technical Report TR-2219-ENV, Apr. 2003, pgs: entire document; Naval Facilities Engineering Command Washington, DC 20374-5065 USA.
International Search Report and Written Opinion for PCT Application No. PCT/US05/15188, mailed Nov. 15, 2005, 2 pages.
International Search Report and Written Opinion for PCT Application No. PCT/US05/15259, mailed Mar. 1, 2006, 3 pages.
International Search Report and Written Opinion for PCT Application No. PCT/US07/02420, mailed Jan. 4, 2008, 4 pages.
International Search Report and Written Opinion for PCT Application No. PCT/US13/33401, mailed Jun. 10, 2013, 20 pages.
Ivanov, M. V. et al. "Additional Oil Production During Field Trials in Russia: Microbial Enhancement of Oil Recovery-Recent Advances " (4th US DOE MEOR Int Conf (Upton, NY, 1992) Proc; Elsevier Develop Petrol Sci Ser No. 39), 1993, pp. 373-381.
Ivanov, M. V. et al. "Die mikrobiologische Bildung von Methan in einer abzubauenden Erdollagerstatte" Frieberger Forschungshefte Reihe C, v., 1982, vol. 389, pp. 189-199.
Johnson et al., 1991, "Preliminary Results of a Coalbed Methane Assessment of the Wind River Indian Reservation, Whoming" Coalbed Methane, pp. 273-284.
Johnson, Ronald C. et al. "A Preliminary Evaluation of Coalbed Methane Resources of the Wind River Indian Reservation, Wyoming" Coal-Bed Methane Potential of the Wind River Indian Reservation, Ed. Stephen Manydeeds, Dec. 1991, pp. 40-64, Bureau of Indian Affairs Division of Energy and Mineral Resources.
Karl Lang, "Coalbed Methane Trends, " PTTC State-of-the-Art Technology Summary, Excerpts in PTTC Network News, 2nd Quarter 2000, http://www.pttc.org/tech_sum/statev6no2.htm, printed Mar. 26, 2004, all pgs.
Kasting, James F. "When Methane Made Climate" Scientific American, Jul. 2004, pp. 80-85.
Kim, Ann G. "Experimental Studies on the Origin and Accumulation of Coalbed Gas" U.S. Dept. of the Interior Bureau of Mines, Report of Investigations 8317, 1978, all pages.
Kim, Ann G. et al. "Hydrocarbon Gases Produced in a Simulated Swamp Environment" U.S. Dept. of the Interior Bureau of Mines, Report of Investigations 7690, 1972, all pages.
Klein, A. et al. "Comparative Analysis of Genes Encoding Methyl Coenzyme M Reductase in Methanogenic Bacteria", Mol Gen Genet, 1988, 213:409-420.
Krumholtz, Lee R. et al. "Confined subsurface microbial communities in Cretaceous Rock" Nature (Mar. 6, 1997) pp. 64-66.
Kunzig, Robert "20,000 Microbes Under the Sea" Mar. 2004, pp. 32-41 , vol. 25, No. 3.
Law, Ben E. et al."Coalbed Gas Accumulations in the Paleocene Fort Union Formation, Powder River Basin, Wyoming" Coalbed Methane—1991; Rocky Mountain Association of Geologists, pp. 179-190.
Le Blanc, Leonard, Artificial Recharge, Offshore, all pgs, Feb. 2000.
L'Haridon, S., Reysenbach, A.L., et al., Hot Subterranean Biosphere in a Continental Oil Reservoir, Nature, v. 377, pp. 223-224, Sep. 21, 1995.
Li, M et al. "Advances in Simulated Tests of Biogas" Oil & Gas Geology, 1996, v. vol. 17, No. 2, pp. 117-122, with abstract.
Lollar, B. Sherwood et al. "Evidence for bacterially generated hydrocarbon gas in Canadian Shield and Fennoscandian Shield rocks" Geochimicaet Cosmochimica Acta vol. 57, pp. 5073-5085 (1993).
Lomans, Bart P. et al. "Isolation and Characterization of Mehanomethylovorans hollandica gen. nov., sp. nov., Isolated from Freshwater Sediment, a Methyltrophic Methanogen Able to Grow on Dimethyl Sulfide and Methanethiol." Applied and Env. Microbiology, Aug. 1999, p. 3641-3650, vol. 65.
Lovely, Derek R. "Deep Subsurface Microbial Processes" Reviews of Geophysics, 33, 3 / Aug. 1995, pp. 365-381.
Lovley, Derek R. et al., "Use of Dissolved H2 Concentrations To Determine Distribution of Microbially Catalyzed Redox Reactions in Anoxic Groundwater," ES&T Research, Eviron. Sci. Technol., vol. 28, No. 7, 1994, pp. 1205-1210.
Luo Hong-Wei et al.: "Differential expression of methanogenesis genes of Methanothermobacter thermoautotrophicus(former Methanobacterium thermoautotrophicum) in pure culture and in cocultures with fatty acid-oxidizing syntrophs": Applied and Environmental Microbiology , vol. 68, No. 3, Mar. 2002 (Mar. 2002), pp. 1173-1179, XPOO2551248 ISSN: 0099-2240.
Luca Technologies, "Tatums—Laboratory Testing," received by the European Patent Office May 14, 2010, 2 pages.

(56) References Cited

OTHER PUBLICATIONS

Magot, Michel et al. "Microbiology of Petroleum Reservoirs" Antonie van Leeuwenhoek, 2000, 77: 103-116.

Mattavelli, L. et al. "Deep Isotopic Light Methane in Northern Italy" Bacterial Gas, Ed. R. Vially, 1992, pp. 121-132.

McDonald, I.R. et al. "Molecular Ecological Analysis of Methanogens and Methanotrophs in Blanket Bog Peat" Microbial Ecology (1999) 38:225-233.

Menking et al., "Rapd Cleanup of Bacterial DNA from Field Samples", Elsevier, Resources, Conservation and Recycling 27 (1999), 179-186.

Middledorp et al., "Enrichment and Properties of a 1,2,4-trichlorobenzene-Dechlorinating Methanogenic Microbial Consortium," Applied and Environmental Microbiology, Apr. 1997, vol. 63, pp. 1225-1229.

Nandi, R et al. "Microbial Production of Hydrogen: An Overview" Critical Reviews in Microbiology, 24 (1): 61-84 (1998).

Nazina, T. N. et al. "Occurrence and Geochemical Activity of Microorganisms in High-Temperature, Water-Flooded Oil Fields of Kazakhstan and Western Siberia" Geomicrobiology Journal, 1995, v. 13, pp. 181-192.

Nazina, T. N. et al. "Microbial Oil Transformation Processes Accompanied by Methane and Hydrogen-Sulfide Formation" Geomicrobiology Journal, 1985, vol. 4, No. 2, pp. 103-130.

Neue, Heinz-Ulrich "Methane Emission from Rice Fields", BioScience, 1993, pp. 466-473, vol. 43, No. 7, downloaded from http://www.ciesin.org/docs/004-032/004-032.html.

Ng, T. K., and Weimer, P. J., "Possible Nonanthropogenic Origin of Two Methanogenic Isolates from Oil-Producing Wells in the San Miguelito Field, Ventura County, California", Geomicrobiology Journal, 1989, v. 7, pp. 185-192.

O'Carroll, Christopher "The Pervasive Presence of Microbes" http://www/umassmag.com/Summer_2003/The_pervasive_presence_of_microbes_5_08.html, 2003, all pages.

Ooteghem et al., "Hydrogen Production by the Thermophilic Bacterium, Thermotogo Neapolitana," Proceedings of the 2001 DOE Hydrogen Program Review, 2001, all pgs.

Orphan et al., "Culture-Dependant and Culture-Independent Characterization of Microbial Assemblages Associated with High-Temperature Petroleum Reservoirs," American Society for Microbiology, pp. 700-711, 2000.

PCT International Search Report and Written Opinion mailed Nov. 5, 2010; International Application No. PCT/US2010/049845; 9 pages.

Panow, A. et al. "Mechanisms of Biologically-Mediated Methane Evolution from Black Coal", Fuel Processing Technology v. 52, pp. 115-125, 1997.

Pedsersen, K. "Exploration of Deep Intraterrestrial Microbial Life: Current Perspectives" FEMS Microbiology Letters 185 (2000) pp. 9-16.

Puri et al. "Enhanced Coalbed Methane Recovery" Proceedings 1990 SPE Annual Technical Conference and Exhibition Reservoir Engineering, Sep. 23-26, 1990, New Orleans, Louisiana, SPE 20732, 1990, pp. 193-202.

Rahman et al., "Towards efficient Crude Oil Degradation by a mixed bacterial consortium," Bioresource Technology, 2002, vol. 85, pp. 257-261.

Reeve, John N. "Archaebacteria Then ... Archaes Now (Are There Really No Archaeal Pathogens?)" Journal of Bacteriology, vol. 181, No. 12, Jun. 1999 pp. 3613-3617.

Revesz, K. et al. "Methane production and consumption monitored by stable H and C isotope ratios at a crude oil spill site, Bemidji, Minnesota" Applied Geochemistry, 1995, vol. 10, pp. 505-515.

Rice, Dudley D. "Controls, habitat, and resource potential of ancient bacterial gas", Bacterial Gas, Ed. Vially, R., 1992, pp. 91-118, Paris.

Rice, Dudley D. et al. "Characterization of coal-derived hydrocarbons and source-rock potential of coal beds, San Juan Basin, New Mexico and Colorado, U.S.A." International Journal of Coal. Geology, 1989, pp. 597-626, vol. 13.

Rice, Dudley D. et al. "Composition and Origins of Coalbed Gas" Hydrocarbons from Coal: American Association of Petroleum Geologists Studies in Geology #38, Eds. Law, B.E., and Rice, D.D., 1993, pp. 159-184.

Rice, Dudley D. et al. "Generation, Accumulation, and Resource Potential of Biogenic Gas" The American Association of Petroleum Geologists Bulletin, vol. 65, No. 1, Jan. 1981, all pgs.

Rice, Dudley D. et al. "Nonassociated Gas Potential of San Juan Basin Considerable" Oil & Gas Journal, Aug. 1990, pp. 60-61, vol. 88, No. 33.

Ridgley, J.L. et al. "Re-Evaluation of the Shallow Biogenic Gas Accumulation, Northern Great Plains, USA—Is the Similar Gas Accumulation in Southeastern Alberta and Southwestern Saskatchewan a Good Analog?" Summary of Investigations (1999) vol. 1 pp. 64-78.

Rightmire, C.T. et al. "Coalbed Methane Resource", 1984, Coalbed methane resources of the United States, AAPG Studies in Geology #17, Tulsa, all pgs.

Rooney-Varga, Juliette N et al. "Microbial Communities Associated with Anaerobic Benzene Degradation in a Petroleum-Contaminated Aquifer", Applied and Environmental Microbiology, v. 65, No. 7, pp. 3056-3063, Jul. 1999.

Rozanova, E.P. et al. "Distribution of Sulfate-Reducing Bacteria Utilizing Lactate and Fatty Acids in Anaerobic Ecotopes of Flooded Petroleum Reservoirs" Institute of Microbiology, Academy of Sciences of the USSR, Moscow. Translated from Mikrobiologiya, vol. 60, No. 2, pp. 360-367, Mar.- Apr. 1991.

Rozanova, E.P. et al. "Microbiological Processes in a High-Temperature Oil Field", Microbiology, v. 70, No. 1, pp. 102-110, 2000.

Schoell, Martin "Genetic Characteristics of Natural Gases" The American Association of Petroleum Geologists Bulletin, Dec. 1983, p. 2225-2238, vol. 67, No. 12.

Schoell, Martin et al. "Natural Sites of Bio-Conversion of CO2 and Hydrocarbons in the Subsurface: San Juan Basin and Michigan Basin" 2001 AAPG Annual Convention, Jun. 3-6, 2001, p. A180, abstract only.

Scott, A.R., Intergas'95, "Limitations and Benefits of Microbiallly Enhanced Coalbed Methane"; May 15-19, 1995-The University of Alabama Tuscaloosa, all p. 1995.

Scott, Andrew R. "Composition and Origin of Coalbed Gases from Selected Basins in the United States" Proceedings of the 1993 International Coalbed Methane Symposium, University of Alabama/Tuscaloosa, May 17-21, 1993; pp. 207-222.

Scott, Andrew R. "Improving Coal Gas Recovery with Microbially Enhanced Coalbed Methane" in Coalbed Methane: Scientific, Environmental and Economic Evaluation; Eds. M. Mastaletcz, M. Glikson, and S. Golding, 1999, pp. 89-110, Kluwer Academic Publishers, Netherlands.

Scott, Andrew R. et al. "A New Energy Resource: Microbially Enhanced Gas Generation" 2001 AAPG Annual Convention, Jun. 3-6, 2001, p. A182, abstract only.

Scott, Andrew R. et al. "Relation between basin hydrology and Fruitland gas composition, San Juan Basin, Colorado and New Mexico" Methane From Coal Seams Technology, Nov. 1991, pp. 10-18, vol. 9, No. 1.

Scott, Andrew R. et al. "Thermogenic and Secondary Biogenic Gases, San Juan Basin, Colorado and New Mexico -- Implications for Coalbed Gas Producibility" AAPG Bulletin, Aug. 1994, v. 78, No. 8, pp. 1186-1209.

Smith, John W. et al. "Microbial Origin of Australian Coalbed Methane" AAPG Bulletin, vol. 80, No. 6 (Jun. 1996), pp. 891-897.

Smith, John W. et al. "The Stable Isotope Geochemistry of Australian Coals" Org. Geochem. Vol. 3, 1982, pp. 111-131.

Springer, E. et al. "Partial Gene Sequences for the A Subunit of Methyl-Coenzyme M Reductase (Mcrl) as a Phylogenetic Tool for the Family Methanosarcinaceae", International Journal of Systematic Bacteriology, 1995, pp. 554-559.

Takashima, M. et al. "Mineral Requirements for Methane Fermentation" Critical Reviews in Environmental Control, vol. 19, Issue 5 (1990) pp. 465-479.

(56) References Cited

OTHER PUBLICATIONS

Ulrich, Glenn A. et al., "Active Biogenesis, Microbes are making natural gas in Wyoming's Powder River Basin", Energy, Spring 2005, XP008128250, pp. 21-26.
Um, Y., "Isolation and characterization of polycyclic aromatic hydrocarbon-degrading microorganisms under methanogenic conditions," Dissertation, University of Maryland, 2004, pp. 1-99.
Van Ginkel, S., et al., "Biohydrogen Production as a Function of PH and Substrate Concentration", Environmental Science and Technology, American Chemical Society, Easton, Pa, USA, vol. 35, No. 24, Dec. 15, 2001, pp. 4726-4730.
Velji, M.I. et al., "The Dispersion of Adhered Marine Bacteria by Pyrophsphate and Ultrasound Prior to Direct Counting", published in IFREMER, Actes de Colloques, 3, 1986, pp. 249-259.
Volkwein, J.C. et al. "Biological Production of Methane from Bituminous Coal", Fuel Processing Technology, v. 40, pp. 339-345, 1994.
Watanabe, K., et al., "Diversity and Abundance of Bacteria in An Underground Oil-Storage Cavity," BMC Microbiology, [online], 2002, [retrieved on Aug. 18, 2011]. Retrieved from: http://www.biomedcentral.com/content/pdf/1471-2180-2-23.pdf.
Weiner, J. M., and Lovley, D. R. "Rapid Benzene Degradation in Methanogenic Sediments from a Petroleum-Contaminated Aquifer", Appl. Environ. Microbiology 1998, vol. 64, No. 5, pp. 1937-1939.
Wellsbury, Peter et al. "Deep Marine biosphere fuelled by increasing organic matter availability during burial and heating" Nature 388, 573-576 (Aug. 7, 1997).
Whitfield, John " Origins of life: Born in a watery commune" Nature, (Feb. 19, 2004) pp. 674-676, vol. 427.
Whiticar, Michael J. "Correlation of natural gases with their sources" In: Magoon L. and W. Dow (eds.) The Petroleum System From Source to Trap, AAPG Spec. Publ. Memoir 60, 1994, Ch. 16, 261-83.
Whiticar, Michael J. et al. "Biogenic methane formation in marine and freshwater environments: CO2 reduction vs. acetate fermentation-Isotope evidence" Geochimica et Cosmochimica Acta, 1986, pp. 693-709, vol. 50, No. 5.
Zajic, J. E. et al., "Microbial Hydrogen Production From Replenishable Resources," Int. J. Hydrogen Engergy, vol. 4, published 1979, pp. 385-402.
Zengler et al., "Methane Formation From Long-Chain Alkanes by Anaerobic Microorganisms," Nature, vol. 401, pp. 266-269, Sep. 16, 1999.
Zobell, C.E., "Bacterial Release of Oil From Sedimentary Materials," The Oil & Gas Journal, pp. 62-65, Aug. 2, 1947.
European Office Action issued Nov. 5, 2010; Application No. 08771271.7; all pages.
European Office Action issued Jul. 10, 2012; Application No. 08771271.7; all pages.
PCT International Search Report and Written Opinion mailed Oct. 1, 2008; International Application No. PCT/US2008/067227; all pages.
PCT International Search Report and Written Opinion mailed May 5, 2010; International Application No. PCT/US2010/028691; all pages.
European Examination Report of EP 05 745 350.8 mailed Mar. 14, 2011, 8 pages.
Hermann, M. et al. "Anaerobic Microflora of Oil Reservoirs: Microbiological Characterization of Samples from Some Production Wells" Bacterial Gas (R. Vially Ed.) Editions Technip. Paris, 1992, pp. 223-233.
Ravot, G. et al., "Fusibacter Paucivorans Gen. Nov., Sp. Nov., an Anaerobic, Thiosulfate-Reducing Bacterium From an Oil-Producing Well," International Journal of Systematic Bacteriology (1999) 49, 1141-1147.
Rice, Dudley D. et al. "Identification and Significance of Coal-Bed Gas, San Juan Basin, Northwestern New Mexico and Southwestern Colorado" Geology and Coal-Bed Methane Resources of the Northern San Juan Basin, Colorado and New Mexico, Ed. J. Fassett, Coal-Bed Methane, San Juan Basin, 1988, pp. 51-59, Rocky Mountain Association of Geologists.
Scott, Andrew R. "Review of Key Hydrogeological Factors Affecting Coalbed Methane Producibility and Resource Assessment" Oklahoma Coalbed-Methane Workshop, 1999, pp. 12-36.
Scott, Andrew R. et al. "Composition, distribution, and origin of Fruitland Formation and Pictured Cliffs Sandstone gases, San Juan basin, Colorado and New Mexico", in S.D. Schwochow, D.K. Murray, and M.F. Fahy, eds., Coalbed methane of western North America: Denver, Rocky Mountain Association of Geologists, 1991, pp. 93-108.
Australian Office Action issued May 2, 2011 for Australian Patent Application No. 2007234895 filed on Apr. 3, 2007, all pages.
Australian Office Action issued Apr. 26, 2013 for Australian Patent Application No. 2011239268 filed on Apr. 3, 2007, all pages.
Australian Office Action issued May 9, 2013 for Australian Patent Application No. 2008265815 filed on Jun. 17, 2008, all pages.
Canadian Office Action issued Mar. 6, 2012 for Canadian Patent Application No. 2,648,752 filed on Apr. 3, 2007, all pages.
Canadian Office Action issued May 26, 2014 for Canadian Patent Application No. 2,691,094 filed on Jun. 17, 2008, all pages.
New Zealand Office Action issued May 18, 2010 for New Zealand Application No. 572426 filed on Apr. 3, 2007, all pages.
New Zealand Office Action issued Aug. 23, 2010 for New Zealand Application No. 572426 filed on Apr. 3, 2007, all pages.
New Zealand Office Action issued Nov. 1, 2010 for New Zealand Application No. 581004 filed on Jun. 17, 2008, all pages.
New Zealand Office Action issued Feb. 25, 2011 for New Zealand Application No. 572426 filed on Apr. 3, 2007, all pages.
New Zealand Office Action issued Mar. 24, 2011 for New Zealand Application No. 581004 filed on Jun. 17, 2008, all pages.
New Zealand Office Action issued May 13, 2011 for New Zealand Application No. 572426 filed on Apr. 3, 2007, all pages.
New Zealand Office Action issued Jun. 13, 2011 for New Zealand Application No. 581004 filed on Jun. 17, 2008, all pages.

* cited by examiner

BIOLOGICALLY ENHANCED OIL RECOVERY METHODS

TECHNICAL FIELD

The present technology relates to oil recovery. More specifically, the present technology relates to enhanced oil recovery from biological methane generation.

BACKGROUND

Increasing world energy demand is creating unprecedented challenges for recovering energy resources, and mitigating the environmental impact of using those resources. Some have argued that the worldwide production rates for oil and domestic natural gas will peak within a decade or less. Once this peak is reached, primary recovery of oil and domestic natural gas will start to decline, as the most easily recoverable energy stocks start to dry up. Historically, old oil fields and coal mines are abandoned once the easily recoverable materials are extracted.

As worldwide energy prices continue to rise, it may become economically viable to extract additional oil and coal from these formations with conventional drilling and mining techniques. However, a point will be reached where more energy is required to recover the resources than can be gained by the recovery. At that point, traditional recovery mechanisms will become uneconomical, regardless of the price of energy.

Thus, there remains a need for improved methods of recovering oil and other carbonaceous materials from formation environments. There also remains a need for methods of introducing chemical amendments to a geologic formation that will stimulate the biogenic production of methane, which may be used to increase oil recovery. These and other needs are addressed by the present technology.

SUMMARY

Methods of enhancing oil recovery may include accessing a consortium of microorganisms in a geologic formation that includes oil. The methods may include delivering an aqueous material incorporating dissolved hydrogen to the consortium of microorganisms. The methods may include increasing production of gaseous materials by the consortium of microorganisms. The methods may also include recovering oil from the reservoir.

In some embodiments the gaseous materials may improve oil flow diversion within the reservoir. The gaseous materials may be or include methane. The aqueous material may be or include water with a dissolved hydrogen content above or about 100 µMoles hydrogen per liter of aqueous material. The dissolved hydrogen content may be maintained below a saturation concentration for hydrogen. The dissolved hydrogen content may be maintained below 50% gas saturation for the aqueous material. The aqueous material may further include incorporated metals, which may be or include compounds including one or more of cobalt, copper, manganese, molybdenum, nickel, tungsten, and zinc. The aqueous material may also include yeast extract. Delivering the aqueous material may include injecting the aqueous material at a pressure greater than or about 3.4 MPa. A temperature of the aqueous material as delivered may be maintained at greater than or about 25° C.

The present technology may also include methods of increasing oil recovery from a reservoir. The methods may include accessing microorganisms in a geologic formation that includes oil. The methods may include detecting a decrease in a production rate of methane from the reservoir that is indicative of a rollover effect. The methods may include injecting an aqueous fluid into the reservoir. The aqueous fluid may be characterized by a dissolved hydrogen concentration of greater than or about 100 µMoles hydrogen per liter of aqueous fluid. The methods may include increasing methane production within the reservoir to a level greater than an inflection point where the rollover effect began to occur. The methods may also include recovering oil from the reservoir.

In some embodiments the methane may improve oil flow diversion within the reservoir. The dissolved hydrogen concentration may be maintained below or about 5,000 µMoles hydrogen per liter of aqueous fluid. Delivering the aqueous fluid may include injecting the aqueous fluid at a pressure greater than or about 7 MPa. A temperature of the aqueous fluid as injected may be maintained at greater than or about 25° C. Native water within the reservoir may be characterized by a sulfate concentration below or about 100 mg per liter of native water. The aqueous fluid may also include incorporated metals. The aqueous fluid may also include yeast extract. The aqueous fluid may be injected to provide a delivery rate of hydrogen between about 7 standard cubic centimeters of dissolved hydrogen per liter of aqueous fluid and about 37 standard cubic centimeters of dissolved hydrogen per liter of aqueous fluid.

Such technology may provide numerous benefits over conventional systems and techniques. For example, by utilizing dissolved hydrogen, delivery to desired microorganism archaea may be improved. Additionally, by limiting the incorporated hydrogen below saturation concentration may control activity of sulfate reducing bacteria. These and other embodiments, along with many of their advantages and features, are described in more detail in conjunction with the below description and attached figures.

BRIEF DESCRIPTION OF THE DRAWINGS

A further understanding of the nature and advantages of the disclosed technology may be realized by reference to the remaining portions of the specification and the figures.

DETAILED DESCRIPTION

Biological methane generation is a common source of methane in oil reservoirs. Because microbes use oil as a source of carbon, they tend to inhabit areas in reservoirs directly at the oil/water interface. In the case of biologically enhanced oil recovery, or BioEOR, microbes may create a local increase in the amount of methane present at this interface. In high pressure portions of the reservoir, methane may be a dissolved gas that rapidly saturates water, and migrates into oil, where it is more soluble. Consequently, in this high pressure environment, methane may act as a solvent for oil, decreasing its viscosity and slightly increasing its size. Both of these factors result in more efficient sweep of oil by water in a waterflood operation, improving the mobility ratio of oil and resulting in greater oil recovery. This may be termed oil or water flow diversion within a reservoir or formation environment.

When methane is generated or migrates in flowing water to a low pressure environment, such as near an oil production well, the confining pressure that keeps methane as a dissolved gas is released, and a small bubble of gas is produced. This may be expected to occur in areas with large volumes of water and very little oil volume, where water may have the least resistance to transport. Because methane at low pressure has little solubility in water, and because it is hydrophobic, the bubble can block pore throats or connections between pore areas. Hydrophobic exclusion forces may be likely to maintain bubbles of methane for long periods of time, so this blockage of water transport may be durable. Water may continue to transport, but this transport may extend into less standard flow patterns, contacting areas of the reservoir that have more oil. Thus, flow diversion of water may result in a larger sweep area in the reservoir, and increase oil recovery. The present technology may enhance oil recovery by increasing production of biological methane within a formation environment, and then utilizing flow diversion to direct oil towards recovery access positions.

Figure 1:
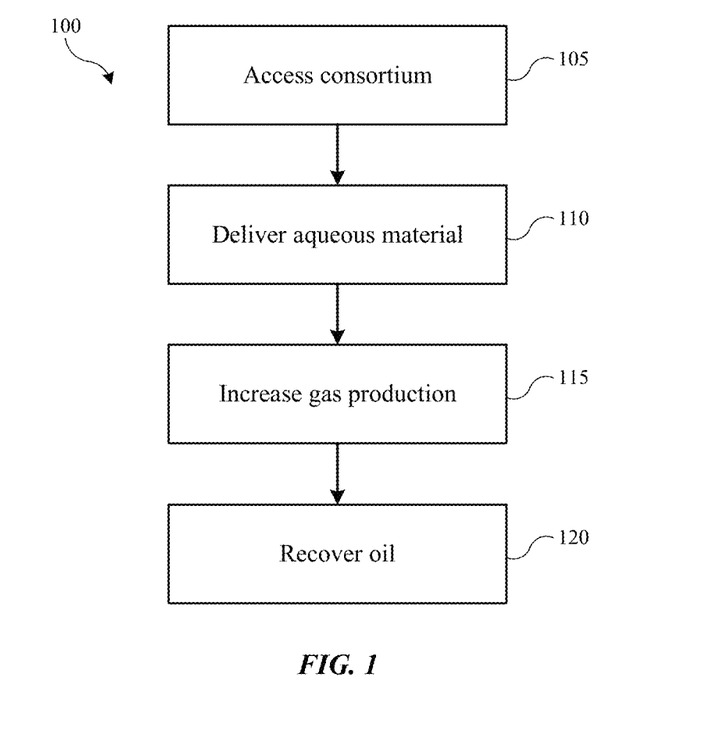
FIG. 1 is a flowchart illustrating exemplary operations in a method of increasing oil recovery from a reservoir according to some embodiments of the present technology.

FIG. 1 illustrates a method 100 of increasing oil recovery from a reservoir or formation environment. The method is designed to stimulate a consortium of microorganisms in the geologic formation to produce methane and other byproducts that may incorporate within oil to improve movement of the oil, such as by reducing viscosity, allowing enhanced oil recovery. The methods performed may stimulate and/or activate a consortium in the formation to start producing the methane, and may increase production of an amount of methane that may be naturally formed within the environment. The methods may further include stopping or decreasing a "rollover" effect such as when the concentration of methane or other metabolic products starts to plateau after a period of monotonically increasing. These and other stimulation effects may be promoted by the materials delivered to the environment according to the method.

The method 100 may include accessing a consortium of microorganisms within the geologic formation at operation 105. The microorganisms may reside in oil, formation water, or at an interface between the fluids. The geologic formation may be a previously explored oil field in which production of oil may have decreased, or for which increased production may be sought. In other embodiments the geologic formation may be a carbonaceous material-containing subterranean formation, such as a coal deposit, natural gas deposit, carbonaceous shale, or other naturally occurring carbonaceous material. In many of these instances, access to the formation can involve utilizing previously mined or drilled access points to the formation. For unexplored formations, accessing the formation may involve digging or drilling through a surface layer to access the underlying site where the microorganisms are located.

Once access to the microorganisms in the formation is available, an aqueous material may be provided to the microorganisms at operation 110. The aqueous material may be a water or other fluid injection, and in embodiments of the present technology, the aqueous material may be modified to incorporate an amount of dissolved hydrogen. At operation 115, production of gaseous materials by the consortium of microorganisms may be increased through metabolizing materials within the aqueous material. These gaseous materials may be or include methane, which as explained above may migrate into oil and increase mobility of the oil. At operation 120, the oil may be recovered from the formation environment. For example, the recovery may be by forced diversion of the oil, which may include a waterflood that may transport the oil to a recovery location. Because the solubilized methane may decrease viscosity of the oil and increase mobility, the present technology may improve oil flow diversion.

The aqueous material may be or include water in some embodiments, and the water may be modified to increase a dissolved hydrogen concentration within the fluid. Some conventional technologies deliver hydrogen concomitantly with the water injection, which provides bubbled hydrogen to the formation environment. This may reduce the availability of the hydrogen to microorganisms within the consortium through egress from the injected fluid. As explained further below, this may additionally increase the overall amount of hydrogen within the formation environment, which may lead to souring and corrosion issues within the formation environment. Accordingly, the present technology may limit the amount of undissolved hydrogen delivered into the formation environment, and in some embodiments may prevent delivery of hydrogen that is not substantially, essentially, or completely dissolved in the aqueous material.

To reduce or limit hydrogen from escaping the aqueous material, the amount of dissolved hydrogen incorporated within the aqueous fluid prior to or at delivery into the formation environment may be maintained below a saturation concentration for hydrogen within the aqueous material. For example, saturation concentration may be affected by the temperature and pressure of the aqueous material. The present technology may operate at increased pressure and temperature compared to conventional technologies, which may increase the saturation concentration of hydrogen within the fluid. Accordingly, in some embodiments the saturation concentration may be up to or about 20,000 µMoles hydrogen per liter of aqueous material, or higher as temperature and pressure are increased. The hydrogen may be delivered into a moving stream of fluid in some embodiments, and may be expressly incorporated as a dissolved gas, and not as bubbles of gas within a fluid stream.

Relatively high hydrogen concentration may also affect the microbial community as will be further explained below, and thus the dissolved hydrogen concentration may be maintained below the saturation concentration, such as below or about 5,000 µMoles per liter of aqueous material, and in some embodiments may be maintained below or about 4,000 µMoles per liter of aqueous material, below or about 3,000 µMoles per liter of aqueous material, below or about 2,000 µMoles per liter of aqueous material, below or about 1,000 µMoles per liter of aqueous material, below or about 900 µMoles per liter of aqueous material, below or about 800 µMoles per liter of aqueous material, below or about 700 µMoles per liter of aqueous material, below or about 600 µMoles per liter of aqueous material, below or about 500 µMoles per liter of aqueous material, below or about 400 µMoles per liter of aqueous material, below or about 300 µMoles per liter of aqueous material, below or about 200 µMoles per liter of aqueous material, below or about 100 µMoles per liter of aqueous material, below or about 50 µMoles per liter of aqueous material, or less.

Below a threshold, hydrogen incorporation may not stimulate or affect the environment, and thus in some embodiments the dissolved hydrogen concentration may be maintained above about 100 µMoles per liter of aqueous material, above about 200 µMoles per liter of aqueous material, above about 300 µMoles per liter of aqueous material, above about 400 µMoles per liter of aqueous material, or more. The dissolved hydrogen concentration may also be stated in terms of a percentage of saturation concentration, and in embodiments the dissolved hydrogen concentration may be maintained below or about 60% of the saturation concentration at a particular temperature or pressure, and in some embodiments the dissolved hydrogen concentration may be below or about 50% of the saturation concentration, below or about 40% of the saturation concentration, below or about 30% of the saturation concentration, below or about 20% of the saturation concentration, below or about 10% of the saturation concentration, below or about 5% of the saturation concentration, or less.

The methods may also include providing one or more additional materials into the formation environment with the aqueous material. For example, a solution or mixture of materials incorporated within water, such as deionized water, may also be delivered. The materials included within the additional materials may include metals, salts, acids, and/or extracts. The salts or materials may be included in any hydrate variety, including monohydrate, dihydrate, tetrahydrate, pentahydrate, hexahydrate, heptahydrate, or any other hydrate variety. Exemplary materials may include metals or metallic compounds including one or more of cobalt, copper, manganese, molybdenum, nickel, tungsten, or zinc. Yeast extract may be included to provide further nutrients to the microorganisms, and may include digests and extracts of commercially available brewers and bakers yeasts. A non-exhaustive list of materials that may be included in any amount or ratio include ammonium chloride, cobalt chloride, copper chloride, manganese sulfate, nickel chloride, nitrilotriacetic acid trisodium salt, potassium diphosphate, sodium molybdate dihydrate, sodium tripolyphosphate, sodium tungstate, and zinc sulfate.

The aqueous materials as well as any of the incorporated materials may be provided to the formation in a single amendment, or they may be provided in separate stages. For example, when both hydrogen and additional materials are used, both the additional materials and the dissolved hydrogen may be incorporated within an aqueous material delivered into the formation environment. Additionally, separate aqueous materials may be delivered into the formation environment with one including the dissolved hydrogen, and another including the additional materials.

Whether the hydrogen and additional materials are introduced to the formation simultaneously or separately, they may be combined in situ and exposed to microorganisms. The combination of the hydrogen and materials can stimulate the microorganisms to increase methane production, which can then solubilize within the oil to increase the mobility and the ability to retrieve the oil.

In some embodiments the methods may also include measuring the concentration of methane prior to recovery of the oil. For gas phase metabolic products, the partial pressure of the product in the formation may be measured, while aqueous metabolic products may involve measurements of molar concentrations. Measurements may be made before providing the amendment, and a comparison of the product concentration before and after the amendment may also be made.

In some embodiments the aqueous material may be delivered within particular temperature and pressure ranges. As noted previously, the aqueous material may be delivered at a relatively increased temperature and pressure, which may increase an amount of dissolved hydrogen, and may also improve incorporation within the formation environment. For example, the aqueous material may be delivered to the formation environment at a temperature above or about 25° C., and in some embodiments the aqueous material may be delivered at a temperature above or about 30° C., above or about 40° C., above or about 50° C., above or about 60° C., above or about 70° C., above or about 80° C., above or about 90° C., or higher. In some embodiments the temperature may be maintained below or about 100° C. or less to limit a temperature affect within the formation environment, such as which may affect the microorganisms. In some embodiments the temperature may be equal to a downhole temperature within the formation that may be measured prior to delivery of the aqueous material.

The aqueous material may be delivered within the formation environment at a pressure that may facilitate distribution within the formation environment, and may ensure adequate entrainment of hydrogen in a dissolved form within the aqueous material. For example, the aqueous material may be maintained at a pressure above or about 0.7 MPa, and in some embodiments the pressure of the aqueous material may be maintained above or about 1 MPa, above or about 2 MPa, above or about 3 MPa, above or about 5 MPa, above or about 7 MPa, above or about 9 MPa, above or about 10 MPa, above or about 12 MPa, above or about 14 MPa, above or about 15 MPa, above or about 16 MPa, above or about 17 MPa, above or about 18 MPa, above or about 20 MPa, or higher.

Figure 2:
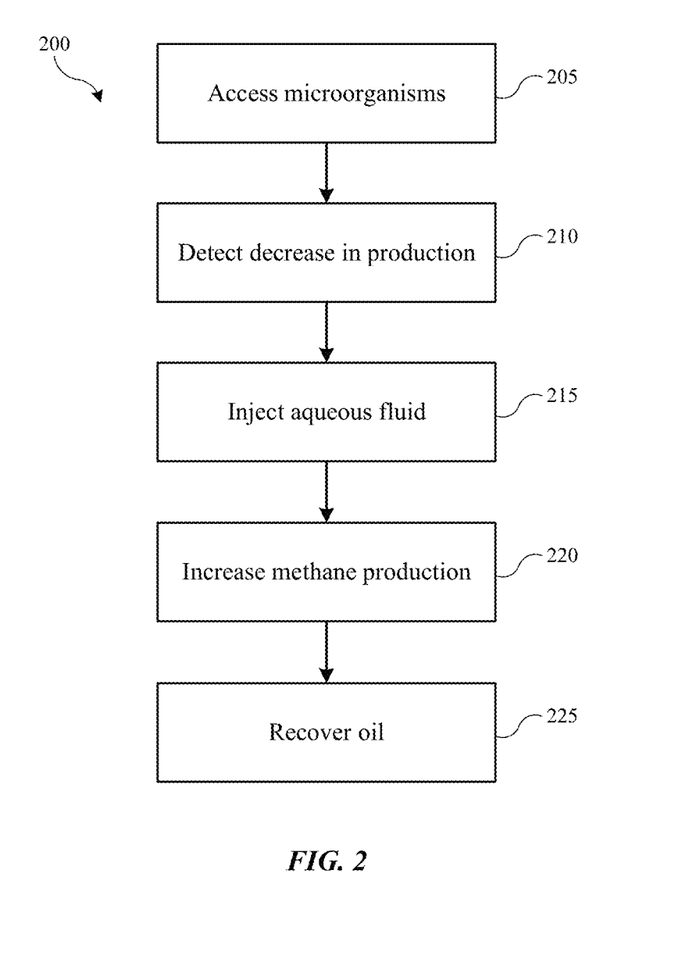
FIG. 2 is a flowchart illustrating exemplary operations in a method of increasing oil recovery from a reservoir according to some embodiments of the present technology.

FIG. 2 illustrates exemplary operations in a method 200 for increasing oil recovery from a reservoir or formation environment. Method 200 may include any of the operations or materials discussed previously with respect to method 100, and may be performed at any of the conditions described above. For example, method 200 may include accessing microorganisms in a geologic formation that includes oil at operation 205. Measurements may be performed to detect a decrease in a production rate of methods from the reservoir at operation 210. This decrease in production may be indicative of a rollover effect. Rollover may be a condition where the rate of biogenic methane production starts to plateau as the in situ methane concentration reaches a certain level. In many instances, the rate flattens to zero, and the methane concentration remains constant over time. The rollover point, or the point where the methane concentration may begin to break from a monotonically increasing state, can vary between microorganism consortia, but appears to be reached in almost all unamended samples of carbonaceous material that have been examined. By providing additional materials in method 200, rollover may be reversed to increase production of methane once again.

Subsequent detection of decreased production, method 200 may include injecting an aqueous fluid into the reservoir at operation 215. The aqueous fluid may be characterized by a dissolved hydrogen concentration of greater than or about 100 µMoles hydrogen per liter of aqueous fluid, although the concentration may be maintained below or about 5,000 µMoles hydrogen per liter of aqueous fluid. The hydrogen may include incorporation and amounts as previously described, and the aqueous fluid may also exhibit any of the previously noted characteristics including temperature or pressure. For example, the aqueous fluid may be maintained and/or injected into the formation environment at a pressure greater than or about 3.4 MPa, such as about 7 MPa, and at any of the previously noted temperatures, such as greater than or about 25° C. The aqueous fluid may also include any of the additional materials previously discussed, and may include incorporated metallic compounds and yeast extract.

The aqueous fluid may be injected to provide a particular delivery rate of hydrogen. For example, in some embodiments the injection may be performed to deliver greater than or about 5 standard cubic centimeters of dissolved hydrogen per liter of aqueous fluid, and may be greater than or about 15 standard cubic centimeters of dissolved hydrogen per liter of aqueous fluid, greater than or about 25 standard cubic centimeters of dissolved hydrogen per liter of aqueous fluid, greater than or about 35 standard cubic centimeters of dissolved hydrogen per liter of aqueous fluid, greater than or about 45 standard cubic centimeters of dissolved hydrogen per liter of aqueous fluid, greater than or about 55 standard cubic centimeters of dissolved hydrogen per liter of aqueous fluid, greater than or about 65 standard cubic centimeters of dissolved hydrogen per liter of aqueous fluid, greater than or about 75 standard cubic centimeters of dissolved hydrogen per liter of aqueous fluid, or higher, although the amount may be configured to limit negative effects as will be described in further detail below.

Method 200 may include increasing methane production within the reservoir at operation 220. This increase may be an increase to a level greater than an inflection point where the rollover effect began to occur. Subsequently, oil may be recovered from the reservoir at operation 225. By increasing methane production and subsequent incorporation into oil, oil flow diversion within the reservoir may be improved.

Any of the methods of the present technology may also include an analysis of the microorganism formation environment, which may include measuring the chemical composition that exists in the environment. This may include an in situ analysis of the chemical environment, and/or extracting gases, liquids, and solid substrates from the formation for a remote analysis.

For example, extracted formation samples may be analyzed using spectrophotometry, NMR, HPLC, gas chromatography, mass spectrometry, voltammetry, and other chemical instrumentation. The tests may be used to determine the presence and relative concentrations of elements like dissolved carbon, phosphorous, nitrogen, sulfur, magnesium, manganese, iron, calcium, zinc, tungsten, cobalt and molybdenum, among other elements. The analysis may also be used to measure quantities of polyatomic ions such as $PO_2^{3-}$, $PO_3^{3-}$, and $PO_4^{3-}$, $NH_4^+$, $NO_2^-$, $NO_3^-$, and $SO_4^{2-}$, among other ions. The quantities of vitamins, and other nutrients may also be determined. An analysis of the pH, salinity, oxidation potential (Eh), and other chemical characteristics of the formation environment may also be performed.

A biological analysis of the microorganisms may also be conducted. This may include a quantitative analysis of the population size determined by direct cell counting techniques, including the use of microscopy, DNA quantification, phospholipid fatty acid analysis, quantitative PCR, protein analysis, or any other identification mechanism. The Identification of the genera and/or species of one or more members of the microorganism consortium by genetic analysis may also be conducted. For example, an analysis of the DNA of the microorganisms may be done where the DNA is optionally cloned into a vector and suitable host cell to amplify the amount of DNA to facilitate detection. In some embodiments, the detecting is of all or part of DNA or ribosomal genes of one or more microorganisms. Alternatively, all or part of another DNA sequence unique to a microorganism may be detected. Detection may be by use of any appropriate means known to the skilled person. Non-limiting examples include 16s Ribosomal DNA metagenomic sequencing; restriction fragment length polymorphism (RFLP) or terminal restriction fragment length polymorphism (TRFLP); polymerase chain reaction (PCR); DNA-DNA hybridization, such as with a probe, Southern analysis, or the use of an array, microchip, bead based array, or the like; denaturing gradient gel electrophoresis (DGGE); or DNA sequencing, including sequencing of cDNA prepared from RNA as non-limiting examples.

Additionally, the effect of the injected materials can be analyzed by measuring the concentration of a metabolic intermediary or metabolic product in the formation environment. If the product concentration and/or rate of product generation does not appear to be reaching a desired level, adjustments may be made to the composition of the amendment. For example, if a particular amendment of aqueous material does not appear to be providing the desired increase in methane production, dissolved hydrogen concentration may be adjusted within the aqueous fluid, or additional or alternative metals or other materials may be incorporated within the aqueous fluid.

Figure 3:
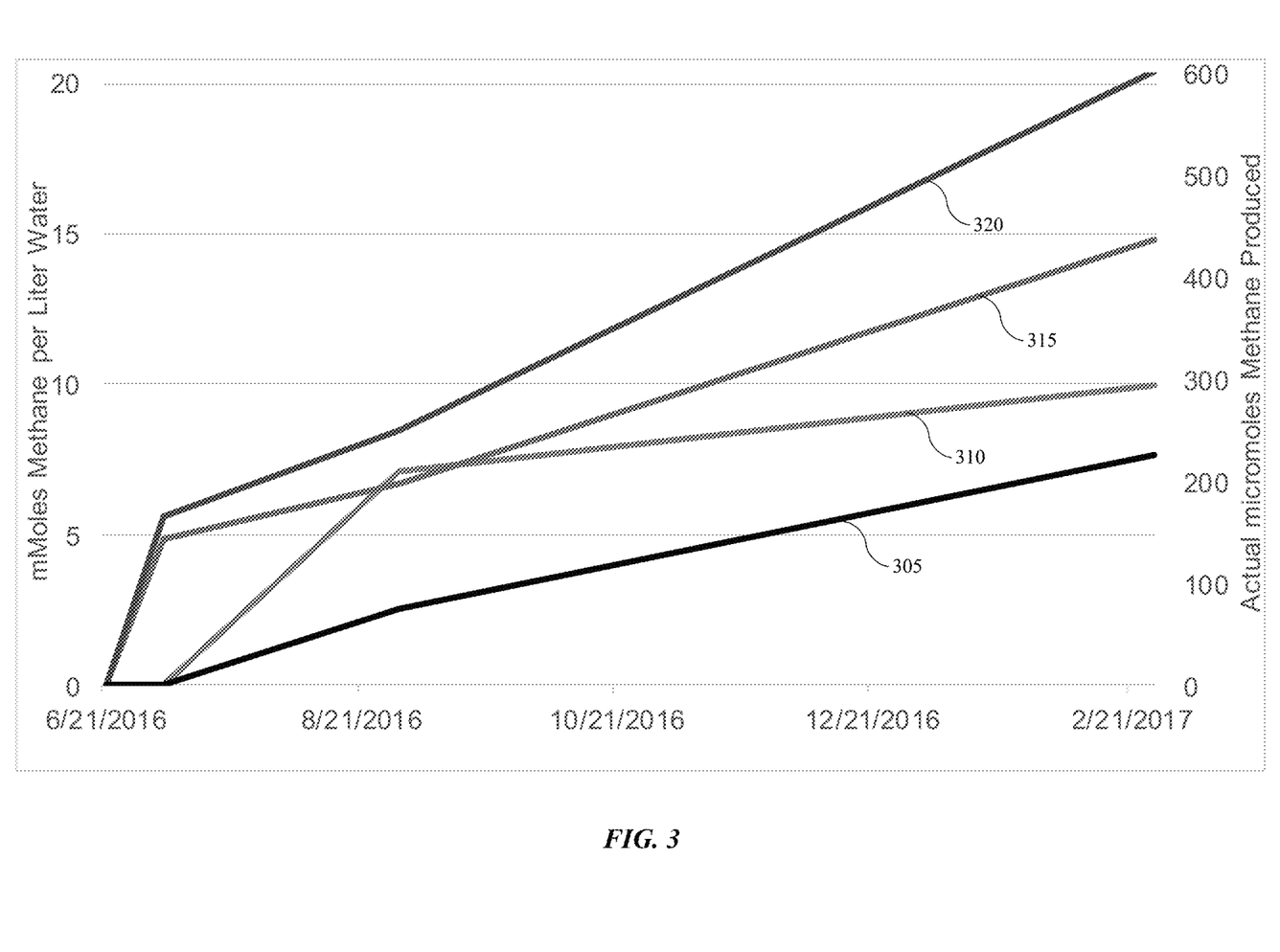
FIG. 3 is a plot of methane production over time in an unamended sample, and samples amended with hydrogen and additional materials according to some embodiments of the present technology

Turning to FIG. 3 is illustrated the effects of amendments provided according to the present technology. As shown in the plot, experiments were run to determine the benefits of hydrogen and additional material incorporation into formation water including microorganisms from the formation environment. In individual trials, tests were run with formation water and microorganisms including unamended oil, oil with incorporated metals and materials, oil with incorporated dissolved hydrogen, and oil with incorporated dissolved hydrogen and additional metals and materials. As illustrated in the plot, line 305 shows the methane formation of unamended oil, which may be similar to a natural formation environment. Line 310 illustrates the incorporation of metals and materials including yeast extract. As illustrated, the additional materials increased methane production, which may increase oil mobility as previously described, and which consequently may increase oil recovery from the formation environment.

Line 315 illustrates incorporation of dissolved hydrogen, which alone surpassed the benefits of metals and additional materials. Finally, line 320 illustrates the combined effect of both dissolved hydrogen incorporation as well as additional materials, which includes all of the previously described materials. Surprisingly, the combination of materials increased the methane production beyond the expected combination of individual incorporation of hydrogen and additional materials illustrated by lines 310 and 315. Accordingly, the combination of dissolved hydrogen and additional materials according to the present technology produced unexpected amounts of methane, which translate to greater oil mobility and enhanced recovery from a formation environment.

Formation analysis may be performed in embodiments of the present technology to limit negative effects of hydrogen augmentation on the microbial community. For example, microorganisms within a consortium may include both methanogens as well as sulfate reducing bacteria. While methanogens may utilize the delivered hydrogen to produce methane, which may beneficially increase oil mobility, sulfate reducing bacteria may cause detrimental effects within the formation environment. Sulfate reducing bacteria may use hydrogen to reduce sulfate into hydrogen sulfide, which may cause souring and corrosion issues within an oilfield or formation environment. The increase in hydrogen sulfide generation may affect the consortium itself, and may reduce the methanogens relative to bacteria, which may then reduce methane production and limit additional oil recovery.

When sulfate is present within the environment, hydrogen amendments may at certain volumes increase the relative abundance of sulfate reducing bacteria in the formation water. This may then increase the rate of sulfate consumption, which may generate additional hydrogen sulfide gas, limiting production by methanogens. These detrimental effects may be related to the amount of sulfate present in the formation environment. The present technology has determined that high concentrations of sulfate, such as greater than or about 100 mg per liter of formation water, may increase the detrimental effects, and limit enhanced oil recovery.

Figure 4:
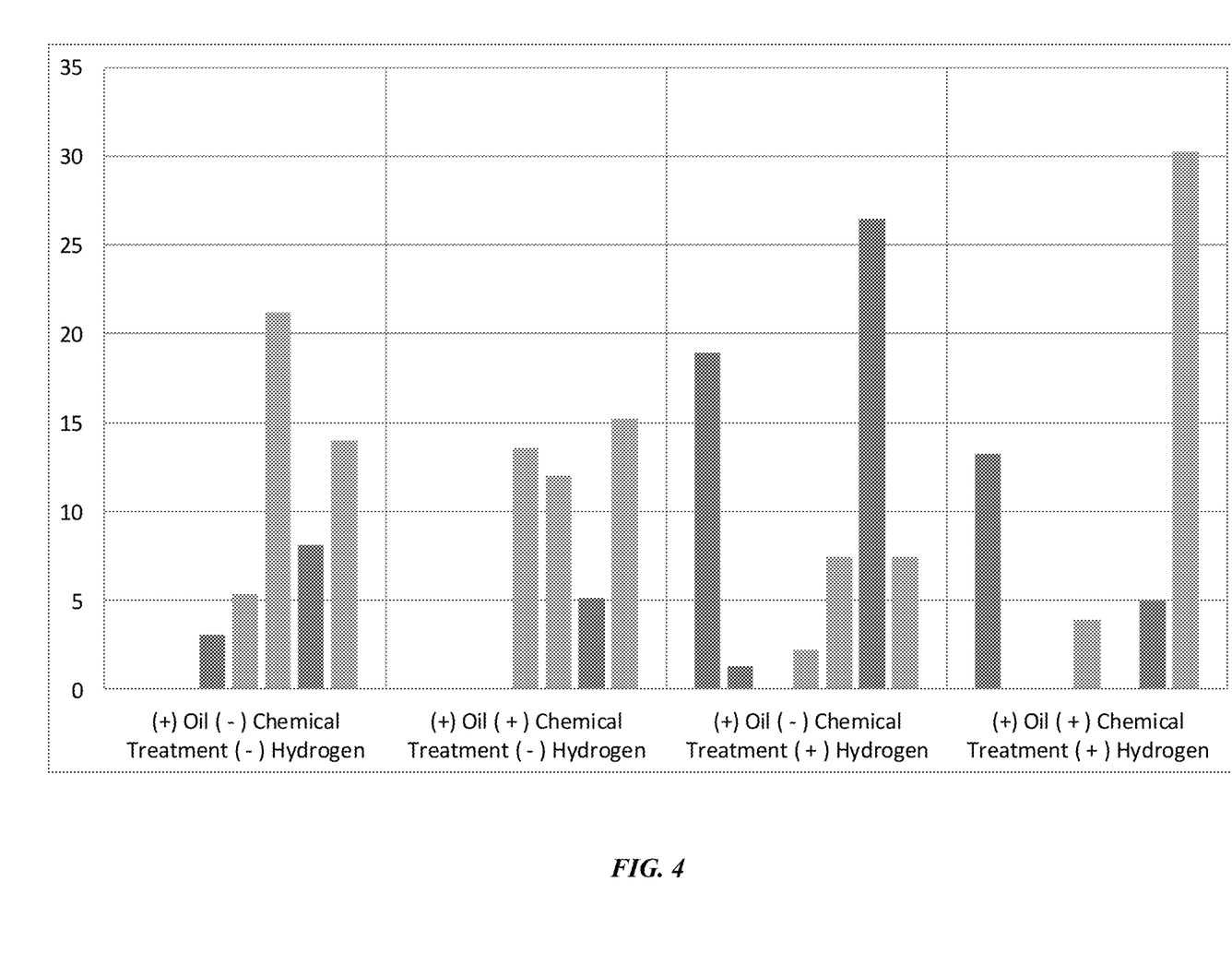
FIG. 4 is a plot of biological changes in a formation environment for an unamended sample, and samples amended with hydrogen and additional materials according to some embodiments of the present technology.

FIG. 4 illustrates the effects of hydrogen and material incorporation on the microorganism community within the formation environment. From left to right are shown unamended formation water and oil, formation water and oil with incorporated metals and additional materials, formation water and oil with incorporated dissolved hydrogen, and finally formation water and oil with incorporated dissolved hydrogen and additional metals and materials. The two bar types include sulfate reducing bacteria as the dark gray bars, and core fermentative bacteria, which feed methanogenesis, as the light gray bars. As shown, the incorporation of dissolved hydrogen alone caused a shift from core fermentative bacteria to sulfate reducing bacteria, which indicates that hydrogen injection can stimulate growth of sulfate reducing bacteria at higher volumes of incorporation. The inclusion of hydrogen and additional metals and materials beneficially increased the amount of fermentative bacteria. Although incorporation of hydrogen produced a shift in sulfate reducing bacteria within the community, experiments showed that in environments characterized by low levels of sulfate within the environment, the rate of sulfate consumption was negligible. Thus, production of hydrogen sulfide and detrimental effects on methanogenic production were limited.

Other experiments showed that the rate of sulfate consumption increased more than two-fold at high sulfate concentration within a formation environment. It is to be understood that the microbial makeup of the consortium may affect the potential negative effects of hydrogen incorporation, and thus hydrogen incorporation may still beneficially increase oil recovery even at high sulfate concentration as methanogens still benefit from hydrogen incorporation. In some embodiments, adjustments in the amount of hydrogen provided may be performed to accommodate sulfate concentration within the environment. Additionally, competition from additional bacteria may further limit increases in sulfate reducing bacteria. However, in some embodiments measurements may be performed on the native formation water within the reservoir to identify a sulfate concentration below or about 100 mg per liter of native formation water in some embodiments.

In the preceding description, for the purposes of explanation, numerous details have been set forth in order to provide an understanding of various embodiments of the present technology. It will be apparent to one skilled in the art, however, that certain embodiments may be practiced without some of these details, or with additional details.

Having disclosed several embodiments, it will be recognized by those of skill in the art that various modifications, alternative constructions, and equivalents may be used without departing from the spirit of the embodiments. Additionally, a number of well-known processes and elements have not been described in order to avoid unnecessarily obscuring the present technology. Accordingly, the above description should not be taken as limiting the scope of the technology.

Where a range of values is provided, it is understood that each intervening value, to the smallest fraction of the unit of the lower limit, unless the context clearly dictates otherwise, between the upper and lower limits of that range is also specifically disclosed. Any narrower range between any stated values or unstated intervening values in a stated range and any other stated or intervening value in that stated range is encompassed. The upper and lower limits of those smaller ranges may independently be included or excluded in the range, and each range where either, neither, or both limits are included in the smaller ranges is also encompassed within the technology, subject to any specifically excluded limit in the stated range. Where the stated range includes one or both of the limits, ranges excluding either or both of those included limits are also included.

As used herein and in the appended claims, the singular forms "a", "an", and "the" include plural references unless the context clearly dictates otherwise. Thus, for example, reference to "a material" includes a plurality of such layers, and reference to "the amendment" includes reference to one or more precursors and equivalents thereof known to those skilled in the art, and so forth.

Also, the words "comprise(s)", "comprising", "contain(s)", "containing", "include(s)", and "including", when used in this specification and in the following claims, are intended to specify the presence of stated features, integers, components, or operations, but they do not preclude the presence or addition of one or more other features, integers, components, operations, acts, or groups.

What is claimed is:

1. A method of increasing oil recovery from a reservoir, the method comprising:
   accessing a consortium of microorganisms in a geologic formation that includes oil;
   delivering a first material comprising incorporated metal or a yeast to the consortium of microorganisms;
   delivering a second aqueous material incorporating dissolved hydrogen to the consortium of microorganisms, wherein the second aqueous material comprises water with a dissolved hydrogen content between about 300 µMoles hydrogen per liter of aqueous material and about 20,000 µMoles hydrogen per liter of aqueous material, wherein the second aqueous material does not include bubbles of hydrogen gas;
   increasing production of gaseous materials by the consortium of microorganisms; and
   recovering oil from the reservoir.

2. The method of increasing oil recovery from a reservoir of claim 1, wherein the gaseous materials improve oil flow diversion within the reservoir.

3. The method of increasing oil recovery from a reservoir of claim 1, wherein the gaseous materials comprise methane.

4. The method of increasing oil recovery from a reservoir of claim 1, wherein the dissolved hydrogen content is maintained below a saturation concentration for hydrogen.

5. The method of increasing oil recovery from a reservoir of claim 1, wherein the dissolved hydrogen content is maintained below 50% gas saturation for the aqueous material.

6. The method of increasing oil recovery from a reservoir of claim 1, wherein the second aqueous material further comprises incorporated metals.

7. The method of increasing oil recovery from a reservoir of claim 6, wherein the incorporated metals include one or more of cobalt, copper, manganese, molybdenum, nickel, tungsten, and zinc.

8. The method of increasing oil recovery from a reservoir of claim 1, wherein the second aqueous material further comprises yeast extract.

9. The method of increasing oil recovery from a reservoir of claim 1, wherein delivering the second aqueous material and first material comprises injecting the aqueous material at a pressure between about 3.4 MPa and about 20 MPa.

10. The method of increasing oil recovery from a reservoir of claim 1, wherein a temperature of the second aqueous material and first material as delivered is maintained at between about 25° C. and about 100° C.

11. The method of claim 1,
the method further comprising:
dissolving hydrogen in water to form the second aqueous material;
delivering the first material and the second aqueous material into a formation,
wherein the first material and the second aqueous material combine in situ to increase the production of gaseous materials by the consortium of microorganisms.

12. A method of increasing oil recovery from a reservoir, the method comprising:
accessing microorganisms in a geologic formation that includes oil;
detecting a decrease in a production rate of methane from the reservoir that is indicative of a rollover effect;
injecting an aqueous fluid into the reservoir, wherein the aqueous fluid is characterized by a dissolved hydrogen concentration of between about 300 µMoles hydrogen per liter of aqueous fluid and about 20,000 µMoles hydrogen per liter of aqueous fluid, wherein the aqueous fluid does not include bubbles of hydrogen gas;
increasing methane production within the reservoir to a level greater than an inflection point where the rollover effect began to occur; and
recovering oil from the reservoir.

13. The method of increasing oil recovery from a reservoir of claim 12, wherein the methane improves oil flow diversion within the reservoir.

14. The method of increasing oil recovery from a reservoir of claim 12, wherein the dissolved hydrogen concentration is maintained below or about 5,000 µMoles hydrogen per liter of aqueous fluid.

15. The method of increasing oil recovery from a reservoir of claim 12, wherein delivering the aqueous fluid comprises injecting the aqueous fluid at a pressure between about 3.4 MPa and about 20 MPa.

16. The method of increasing oil recovery from a reservoir of claim 12, wherein a temperature of the aqueous fluid as injected is maintained at between about 25° C. and about 100° C.

17. The method of increasing oil recovery from a reservoir of claim 12, wherein native water within the reservoir is characterized by a sulfate concentration between about 100 mg per liter of native water and about 0 mg per liter of native water.

18. The method of increasing oil recovery from a reservoir of claim 12, wherein the aqueous fluid further comprises incorporated metals.

19. The method of increasing oil recovery from a reservoir of claim 12, wherein the aqueous fluid further comprises yeast extract.

20. The method of increasing oil recovery from a reservoir of claim 12, wherein the aqueous fluid as injected provides a delivery rate of hydrogen between about 5 standard cubic centimeters of dissolved hydrogen per liter of aqueous fluid and about 40 standard cubic centimeters of dissolved hydrogen per liter of aqueous fluid.

\* \* \* \* \*